United States Patent [19]

Kunugiza et al.

[11] Patent Number: 4,717,697
[45] Date of Patent: Jan. 5, 1988

[54] METHOD OF REGENERATING ZEOLITE TO REMOVE ACETONE AND WATER

[75] Inventors: Kiyomitsu Kunugiza; Tadaaki Yamamoto; Hitoshi Sawada, all of Yamaguchi, Japan

[73] Assignee: Takeda Chemical Industries, Ltd., Osaka, Japan

[21] Appl. No.: 883,120

[22] Filed: Jul. 8, 1986

[30] Foreign Application Priority Data

Jul. 16, 1985 [JP] Japan .................... 60-157572

[51] Int. Cl.⁴ .................... B01J 29/38; B01J 38/04; B01D 53/04; C07C 45/79
[52] U.S. Cl. ........................ 502/34; 34/9; 34/15; 55/33; 55/35; 55/75; 502/56; 568/411
[58] Field of Search .......... 502/34, 56, 515; 34/9-15; 55/33-35, 75; 568/411

[56] References Cited

U.S. PATENT DOCUMENTS 4,373,935  2/1983  Ausikaitis et al. .................... 55/33

FOREIGN PATENT DOCUMENTS 51033    4/1980  Japan ............................ 568/411
1264481  2/1972  United Kingdom ............ 568/411
1346560  2/1974  United Kingdom .
2132910  7/1984  United Kingdom .

*Primary Examiner*—Paul E. Konopka
*Attorney, Agent, or Firm*—Wegner & Bretschneider

[57] ABSTRACT

A method of regenerating hydrous zeolite which contains acetone as well as water after having been used to dehydrate hydrous acetone of the invention which comprises: placing the hydrous zeolite in a closed system in which a heated inert gas is circulated at a pressure more than atmospheric pressures to bring the inert gas into contact with the hydrous zeolite to remove the acetone and water from the zeolite, and condensing the acetone and water in the closed system and removes them from the closed system.

The method is in particular useful for regenerating hydrous zeolite which has been used to dehydrate hydrous acetone resulting from the reaction of L-sorbose with acetone to produce diacetone-L-sorbose, and which thus contains acetone as well as about 1000-4000 ppm of water therein.

3 Claims, 1 Drawing Figure

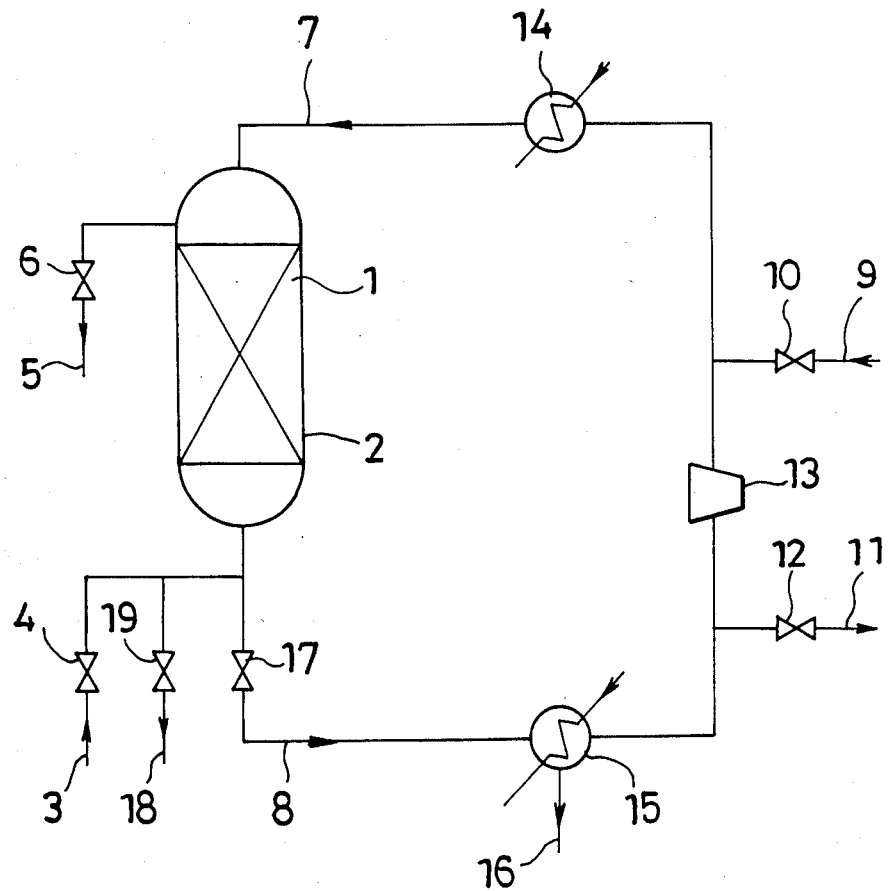

METHOD OF REGENERATING ZEOLITE TO REMOVE ACETONE AND WATER

This invention relates to a method of regenerating hydrous zeolite, and more particularly to a method of regenerating hydrous zeolite which has been used to dehydrate hydrous acetone, and thus contains acetone as well as water.

A distillation method is known to be useful to remove water from hydrous acetone, however, a dehydration of hydrous acetone to water content of about 2000–3000 ppm is an economical limit in industrial applications. Dehydration by water adsorption with zeolite is more advantageous for obtaining acetone hydrated to a higher degree since the method provides the hydrated acetone of water content as low as about 10–200 ppm, as described in Japanese Published Unexamined Patent Application No. 48-52714. It is also known that zeolite is useful for purifying and drying of 1,1,1-trichloroethane, and a method of regenerating the zeolite after such a use with heated inert gases is disclosed in Japanese Published Unexamined Patent Application No. 50-158600.

The hydrous zeolite after having been used for dehydration of hydrous acetone is usually regenerated by heating it to desorb the adsorption water and acetone from the zeolite. For instance, Japanese Published Unexamined Patent Application No. 58-131134 discloses a method of regenerating hydrous zeolite by passing a heated gas downwardly through a column having hydrous zeolite filled therein. However, when the hydrous zeolite containing acetone as well as water is heated, acetone tends to be converted to high boiling point products such as diacetone alcohol and mesityl oxide by the catalysis due to the basicity of the zeolite, and these compounds, when produced, adhere onto the zeolite to cause the deterioration of the properties of zeolite, such as water-adsorption power and mechanical strength. No economical and practical method has hitherto been proposed to regenerate the hydrous zeolite which also contains acetone unstable under the basicity of zeolite without the deterioration of the properties of zeolite.

The inventors have made an extensive study to solve the difficulties involved in the regeneration of hydrous zeolite, and have found out an economical method of regenerating hydrous zeolite without the deterioration of properties, such as adsorption power and strength, by the use of a small amount of inert gases.

An object of the invention is therefore to provide a method of regenerating hydrous zeolite which is economically and advantageously applicable to dehydration of hydrous zeolite.

A specifically important object of the invention is to provide a method of regenerating hydrous zeolite which has been used to dehydrate hydrous acetone and thus contains acetone as well as water therein.

A method of regenerating hydrous zeolite which contains acetone as well as water after having been used to dehydrate hydrous acetone of the invention comprises: placing the hydrous zeolite in a closed system in which a heated inert gas is circulated at a pressure more than atmospheric pressures to bring the inert gas into contact with the hydrous zeolite to remove the acetone and water from the zeolite, and condensing the acetone and water in the closed system and then removing them from the closed system.

Other features and advantages of the invention will be apparent from the following description taken in connection with the accompanying drawing; the single figure is a simplified schematic illustration of an apparatus preferably usable in the invention.

The method of the invention is applicable to dehydration of any zeolite which has been used to dehydrate hydrous acetone in usual manners in chemical industries. Such zeolites usually have an average pore size of about 3–4 Angstrom. Examples of such zeolite include Zeoram 3ASG (Toyo Soda K.K., Japan), Molecular Sieve 3A (Union Showa K.K., Japan), Mizuka Sieves 4A–15P No. 6 (Mizusawa Kagaku Kogyo K.K., Japan), etc.

Meanwhile, examples of cases wherein such hydrous acetone is formed include ketalization of carbohydrates by the use of acetone, e.g., a reaction of L-sorbose with acetone to produce diacetone-L-sorbose, which is an important intermediate in the production of L-ascorbic acid or vitamin C. The reaction of L-sorbose with acetone to produce diacetone-L-sorbose is an equilibrium reaction, as is well known, so that the reaction needs a large amount of anhydrous acetone to proceed, and after the reaction, hydrous acetone is formed. In the industrial production of diacetone-L-sorbose, therefore, it is important from a view point of process economy to recover and dehydrate the hydrous acetone from the resultant reaction mixture for the reuse of acetone in the reaction, since a huge amount of anhydrous acetone is used in the reaction and a huge amount of hydrous acetone is formed after the reaction in the industrial production of diacetone-L-sorbose. Apparently as a result, a huge amount of hydrous zeolite is formed after the dehydration of the hydrous acetone formed as above.

The method of the invention is in particular advantageously applicable to the dehydration of such hydrous zeolite as formed in the way as above which thus contains water in amounts of about 1000–4000 ppm, since the method makes it possible for the hydrous zeolite to be dehydrated by the use of a small amount of inert gases without the deterioration of the zeolite, as will be fully described later. The method is also applicable to the dehydration of hydrous zeolite which contains impurities such as diacetone alcohol, mesityl oxide or phorone together with acetone.

Any inert gas is usable in the invention provided that it is chemically inert to the dehydration of hydrous zeolite at elevated temperatures. Nitrogen, carbon dioxide, argon or helium, for example, are preferably used, and nitrogen is most preferred in the invention.

In the method of the invention, the inert gas is circulated in a closed system which includes therein a column of the hydrous zeolite at a pressure more than atmospheric pressure, e.g., about 0.1–20 kg/cm$^2$G and at a linear velocity of about 0.1–5 m/sec. by the use of blowers, to bring the gas into contact with the hydrous zeolite in the column, thereby to dehydrate and regenerate the zeolite. It is undesirable to circulate the inert gas in the closed system under a pressure less than atmospheric pressure since under such conditions the leakage of the air into the closed system may take place and there results a possibility of explosion of mixed vapor of acetone and the air. On the other hand, when the inert gas has too small a linear velocity in the column, the hydrous zeolite will not be provided with heat sufficient to remove acetone and water therefrom, whereas when the inert gas has too large a linear velocity in the column, there will arise a large pressure drop across the column, which will make the method uneconomical for practical use.

The method of the invention will be now fully set forth with reference to the FIGURE, in which an adsorption column 1 has zeolite 2 filled therein and the column has an inlet 3 operated by a valve 4 for feeding hydrous acetone into the column to dehydrate the hydrous acetone with the zeolite, and an outlet 5 operated by a valve 6 for letting out the dehydrated acetone. In the dehydration step of the hydrous acetone, the valve 4 and 6 are opened to introduce the hydrous acetone through the inlet 3 into the column to dehydrate the hydrous acetone, and the thus dehydrated acetone runs out from the column through the outlet 5. When the zeolite has lost its dehydration power, the valves 4 and 6 are closed to conclude the dehydration step.

The system further includes pipes, namely, an upstream pipe 7 and a downstream pipe 8 with respect to the column 1, respectively, which are connected to each other to construct the closed system. The closed system has an inlet 9 operated by a valve 10 for introducing an inert gas thereinto, a regulating gas outlet 11 operated by a valve 12 so as to release the inert gas from the system, when necessary, to keep the inside the system at a constant pressure predetermined, and a blower 13 to circulate the inert gas in the closed system. Further the closed system has a gas heater 14 on the upstream pipe 7, while on the downstream pipe 8 a gas cooler 15 having an outlet 16 of condensates formed therein to remove it from the system, and a valve 17, as well as an outlet 18 operated by a valve 19.

In the regenerating step of the hydrous zeolite in the column, the valves 10 and 19 are first opened to introducing the inert gas from the inlet 9 into the pipe line to force out the acetone which remains in the column 1 through the outlet 18, and then replacing the atmosphere inside the column by the inert gas. The zeolite thus has acetone thereon in amounts of about 15-35% by weight and water adsorbed thereon in amounts of about 7-15% by weight based on the zeolite, respectively.

Then the valves 10 and 19 are closed, and the valve 17 is opened to circulate the inert gas in the closed system by the blower 13. During being circualted, the inert gas is heated with the gas heater 14 and then is made to come into contact with the hydrous zeolite in the column to evaporate the acetone on the zeolite as well as to desorb the water from the zeolite. Then the inert gas is introduced into the gas cooler 15 where the acetone and water are condensed and removed from the inert gas, and are taken out of the closed system through the outlet 16. The inert gas is in this way circulated in the closed sysem.

In a preferred embodiment of the invention, the regenerating step is composed of the first stage and second stage. In the first stage, the inert gas is heated to a relatively low temperature which is however sufficient to evaporate the acetone on the hydrous zeolite, and is then made to bring into contact with the hydrous zeolite to evaporate the acetone, which is removed by the gas cooler. In the second stage, the inert gas is heated to a higher temperature sufficient to desorb the water from the hydrous zeolite, made to bring into contact with the zeolite to desorb the water therefrom, which is also removed from the closed system. This two stage contact of the inert gas with the hydrous zeolite makes it possible to repress the production of undesired high boiling point products of acetone, thereby to advantageously prevent the deterioration of water adsorption power and mechanical strength of the zeolite generated.

In more detail, in the first stage for the evaporating the acetone, the zeolite is heated to temperatures higher than the boiling point of acetone under the pressure of the closed system but is lower than the carbonizing temperature of acetone by the heated inert gas. Usually the zeolite is heated to temperatures of about 60°-120 C., while the inert gas is circulated at a linear velocity in the column of about 0.1-5 m/sec., preferably about 0.5-2 m/sec., at standard conditions.

The inert gas thus containing acetone after having passed through the zeolite in the column is then introduced into the gas cooler 15 through the downstream pipe 8 to condense the acetone and remove it from the outlet 16 to the outside of the closed system. In the gas cooler, the inert gas is preferably cooled so that it contains uncondensed acetone in amounts of not more than about 300 mg/l, most preferably about 100 mg/l by the cooler. This may be accomplished by cooling the inert gas to temperatures of about −5° C. to 40° C. Even if acetone produces high-boiling temperature products when the hydrous zeolite is heated, these products are also condensed together with acetone in the gas cooler, so that no increase of the concentration of such by-products in the inert gas takes place during the first stage to maintain the concentration in the inert gas at such a low level as causes no deterioration of properties of zeolite, that is, usually about 5-10 mg/l.

Any cooling medium may be usable in the gas cooler in the first stage depending upon the cooling temperature, and sea water or industrial water, for example, may be usable as the cooling medium.

In the following second stage, the inert gas is heated to higher temperatures, preferably about 200°-250° C., and is forced to pass through the zeolite in the column at the same linear velocity as in the first stage to desorb the water from the zeolite. The inert gas thus containing water after the contact with the zeolite is introduced into the gas cooler 15 to condense the water therein and let out from the outlet 16. The inert gas is cooled usually to temperatures of from about −5° C. to 40° C. with such a cooling medium as hereinbefore mentioned. After the removal of water in this way, the inert gas is again heated by the gas heater 14, and is circulated in the closed system.

After the dehydration of the zeolite, the gas heater 14 is stopped. Then the inert gas of temperatures from about −5° C. to about 40° C. is made to bring into contact with the zeolite to cool the zeolite, cooled by the gas cooler 15, and is circulated in this way in the closed system, thereby to cool the zeolite to about 30°-50° C., to the conclusion of the regeneration of the zeolite.

Throughout the removing operations of acetone and water from the zeolite, the inert gas may be in part released from the outlet 11 operated by the valve 12 to keep the inside the closed system at a constant positive pressure predetermined, and in the cooling step of zeolite after the dehydration, a small amount of inert gas may be afresh introduced from the inlet 9 operated by the valve 10 into the closed system to keep the inside the closed system at a constant positive pressure predetermined.

According to the invention, the hydrous zeolite which contains acetone as well as water after having been used to dehydrate hydrous acetone can be regenerated without the deterioration of properties such as water adsorption power and durability with a small amount of inert gas. Usually the amount of inert gas necessary for one batch regeneration of hydrous zeolite in an adsorption column is within the range of only about 2–10 times the total volume of the column and pipes forming the closed system.

In particular, since the inert gas is circulated in the closed system in the method of the invention, only the addition of a small amount of fresh inert gas to the closed system is necessary to keep the inside the closed system at a constant pressure, depending upon the change of temperatures of inert gas circulated therein. Therefore, the method is specifically useful for industrial regeneration of hydrous zeolite formed in a huge amount by the dehydration of hydrous acetone resulting from the industrial production of acetone-L-sorbose.

The invention will be understood more readily with reference to the following examples; however, these examples are intended to illustrate the invention only and are not to be construed as limitation to the invention.

EXAMPLE 1

Zeolite (Zeoram 3ASG by Toyo Soda K.K.) was filled in a column of 25 mm in inner diameter and 1350 mm in height to form an adsorption column. Acetone containing water in amounts of 3000 ppm was passed through the column until the zeolite lost its dehydration power.

As described hereinbefore with reference to the figure, nitrogen gas of 120° C. was passed through the column at a pressure of 0.3 kg/cm$^2$G with a circulating rate of 1.5 m$^3$/hr. or at a superficial velocity of 0.85 m/sec., and then the gas was cooled to from about $-20°$ C. to about 0° C. by a gas cooler to condense and recover the acetone contained in the gas.

Then when the gas came to have a temperature of 60° C. at the outlet of the column, the gas was heated to 230° C. and was passed through the column, and then was cooled to about 30°–35° C. by a gas cooler to condense and recover the water contained in the gas. When the gas came to have a temperature of 200° C. at the outlet of the column, the gas of 35° C. was circulated to cool the zeolite until the gas came to have a temperature of 40° C. at the outlet of the column.

Taking the above series of operations as one cycle, 30 cycles of operations were carried out. The amount of nitrogen used, and the water adsorption power, mechanical strength and crystallinity of the thus regenerated zeolite are shown in Table 1.

TABLE 1

| Cycles | Adsorption Power[1] (% by wt.) | Compressive Strength (kg) | X-Ray Analysis | Nitrogen Used (N1)[2] |
|---|---|---|---|---|
| Control[3] | 19.0 | 1.6 | Base | — |
| 15 | 18.6 | 1.4 | No deterioration | 2.3 |
| 30 | 18.4 | 1.4 | No deterioration | 2.6 |

[1]Adsorption power of water in % by weight based on the zeolite.
[2]At standard conditions.
[3]Before the use for dehydration of hydrous acetone.

As apparent from the above results, the hydrous zeolite was regenerated by the use of small amounts of nitrogen gas.

EXAMPLE 2

Zeolite (Molecular Sieve 3A by Union Showa K.K.) was filled in the same column as in Example 1 to form an adsorption column. Acetone containing water in amounts of 3000 ppm was passed through the column until the zeolite lost its dehydration power.

The resultant hydrous zeolite was regenerated in the same manner as in Example 1 by carrying out 20 cycles of operations. The amount of nitrogen used, and the water adsorption power, mechanical strength and crystallinity of the thus regenerated zeolite are shown in Table 2.

TABLE 2

| Cycles | Adsorption Power[1] (% by wt.) | Compressive Strength (kg) | X-Ray Analysis | Nitrogen Used (N1)[2] |
|---|---|---|---|---|
| Control[3] | 21.0 | 4.0 | Base | — |
| 10 | 20.1 | 3.7 | No deterioration | 2.5 |
| 20 | 20.0 | 3.6 | No deterioration | 2.7 |

[1]Adsorption power of water in % by weight based on the zeolite.
[2]At standard conditions.
[3]Before the use for dehydration of hydrous acetone.

EXAMPLE 3

The same hydrous zeolite was regenerated in the same manner as in Example 1 except that the nitrogen gas was circulated at a circulating rate of 1.0 m$^3$/hr. or a superficial velocity of 0.57 m/sec. under a pressure of 2.0 kg/cm$^2$G.

The amount of nitrogen used, and the properties of the regenerated zeolite are shown in Table 3.

TABLE 3

| Cycles | Adsorption Power[1] (% by wt.) | Compressive Strength (kg) | X-Ray Analysis | Nitrogen Used (N1)[2] |
|---|---|---|---|---|
| Control[3] | 19.0 | 1.6 | Base | — |
| 10 | 18.6 | 1.5 | No deterioration | 5.9 |
| 20 | 18.5 | 1.5 | No deterioration | 6.2 |

[1]Adsorption power of water in % by weight based on the zeolite.
[2]At standard conditions.
[3]Before the use for dehydration of hydrous acetone.

EXAMPLE 4

Zeolite (Mizuka Sieves 4A-15P No. 6 by Mizusawa Kagaku Kogyo K.K.) was filled in the same column as in Example 1 to form an adsorption column. Acetone containing water in amounts of 3000 ppm was passed through the column until the zeolite lost its dehydration power.

The resultant hydrous zeolite was regenerated in the same manner as in Example 1 except that nitrogen gas was circulated at a pressure of 9 kg/cm$^2$G at a circulating rate of 0.5 m$^3$/hr.

The amount of nitrogen used, and the properties of the regenerated zeolite are shown in Table 4.

TABLE 4

| Cycles | Adsorption Water[1] (% by wt.) | Compressive Strength (kg) | Nitrogen Used (N1)[2] |
|---|---|---|---|
| Control[3] | 21.1 | 3.9 | — |

TABLE 4-continued

| Cycles | Adsorption Water[1] (% by wt.) | Compressive Strength (kg) | Nitrogen Used (Nl)[2] |
|---|---|---|---|
| 20 | 19.4 | 3.1 | 14.6 |

[1]Adsorption power of water in % by weight based on the zeolite.
[2]At standard state.
[3]Before the use for dehydration.

COMPARATIVE EXAMPLE

Without circulating, nitrogen gas was passed through the same column as in Example 1 having the same hydrous zeolite as used in Example 1 at a pressure of 0.2 kg/cm$^2$G under the otherwise same conditions as in Example 1.

When 10 cycles of operations were carried out, the amount of nitrogen gas used was 18800 Nl, and when 20 cycles of operations, the amount of nitrogen gas used was 19300 Nl, illustrating that a by far larger amount of nitrogen gas was needed than in the method of invention.

What is claimed is:

1. A method of regenerating hydrous zeolite which contains acetone as well as water after having been used to dehydrate hydrous acetone which comprises: placing the hydrous zeolite in a closed system in which a heated inert gas is circulated at a pressure more than atmospheric pressure to bring the inert gas into contact with the hydrous zeolite to remove the acetone and water from the zeolite, and condensing the acetone and water in the closed system and removing them from the closed system, wherein the hydrous zeolite is regenerated in two stages composed of the first and second stage in which in the first stage the inert gas is heated to a temperature of about 60°–120° C. to evaporate the acetone on the zeolite to remove the acetone, and in the second stage the inert gas is heated to a temperature of about 200°–250° C. to desorb the water from the zeolite.

2. The method as claimed in claim 1 wherein the inert gas is circulated in the closed system at a linear velocity of about 0.1–5 m/sec. under a pressure of 0.1–20 kg/cm$^2$G.

3. The method as claimed in claim 1 wherein the inert gas is nitrogen gas.

* * * * *